United States Patent [19]

Cavalla

[11] 4,356,185
[45] Oct. 26, 1982

[54] THIAZOLES
[75] Inventor: John F. Cavalla, Isleworth, England
[73] Assignee: John Wyeth & Brother Limited, Maidenhead, England
[21] Appl. No.: 247,461
[22] Filed: Mar. 25, 1981
[30] Foreign Application Priority Data
  Apr. 3, 1980 [GB]  United Kingdom ............... 8011251
  Apr. 26, 1980 [GB]  United Kingdom ............... 8013860
[51] Int. Cl.³ ................. C07D 233/54; A61K 31/425
[52] U.S. Cl. ................................ 424/270; 548/203; 548/204
[58] Field of Search ............... 260/245.2 R; 548/204, 548/203, 202; 424/270

[56] References Cited
FOREIGN PATENT DOCUMENTS
  1145884  3/1969  United Kingdom .

OTHER PUBLICATIONS
J. Med. Chem., (1974), vol. 17, pp. 1177 to 1188.

Primary Examiner—Nicholas S. Rizzo
Attorney, Agent, or Firm—Richard K. Jackson

[57] ABSTRACT

The invention concerns compounds of formula

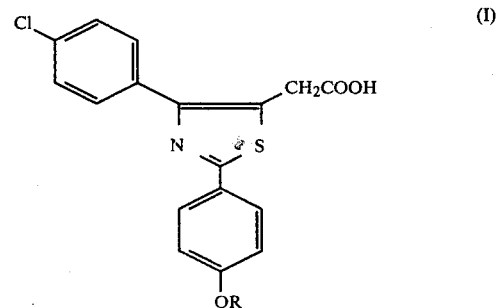

(I)

or salts thereof, wherein R represents an acyl group which possess anti-inflammatory activity and have low toxicity. Methods for preparing the compounds and pharmaceutical compositions are also disclosed.

5 Claims, No Drawings

THIAZOLES

This invention relates to thiazoles, possessing pharmaceutical activity, to processes for preparing them, to pharmaceutical compositions containing them, and to methods of using them.

In our UK Patent Specification No. 1,145,884 there are described and claimed compounds of the general formula (A)

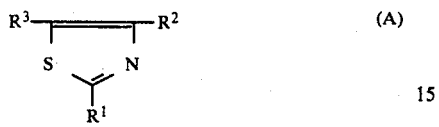

and acid addition salts thereof, in which $R^1$ and $R^2$ are the same or different and are substituted aryl radicals (which may be heteroaryl radicals) and $R^3$ is a lower aliphatic carboxylic acid radical containing from 2 to 6 carbon atoms or a salt, ester, amide, nitrile or hydroxamic acid derivative thereof, said radical $R^3$ being attached to the thiazole ring by a carbon atom on the aliphatic chain.

According to UK Patent Specification No. 1,145,884 the compounds of formula A possess pharmacological activity particularly anti-inflammatory activity. Examples of $R^1$ and $R^2$ are unsubstituted phenyl and phenyl substituted by halogen, lower alkyl, lower alkoxy, nitro, amino, substituted amino, mercapto, alkylthio, alkylsulphonyl, or trihalomethyl.

The anti-inflammatory activity of specific compounds of formula A against carrageenin-induced edema in the rat hind paw was extensively reported by Brown et al, in Journal of Medicinal Chemistry, 1974, Vol. 17 No. 11, pps. 1177 to 1181. Structure activity relationship revealed that the anti-inflammatory activity was found to be optimised when $R^2$ was 4-chlorophenyl. However, the preferred $R^1$ group was found to be phenyl and 4-substitution of this ring reduced the antiinflammatory activity. Thus 4-methoxy and 4-carboxy substitution both substantially reduced activity when $R^2$ was 4-chlorophenyl.

We have now surprisingly found a series of thiazole-5-acetic acids not specifically mentioned in the general formula (A) wherein $R^1$ represents a 4-substituted-phenyl, which possess marked anti-inflammatory activity, especially when administered topically. Furthermore this series of thiazole-5-acetic acids possess low toxicity.

Accordingly this invention provides a compound having the formula:

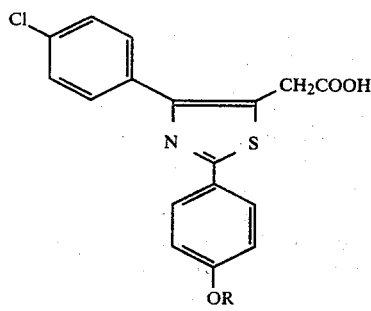

and salts thereof wherein R represents an acyl group, e.g. an alkanoyl group having 2 to 7 carbon atoms, preferably 2 to 5 carbon atoms. Examples of R are acetyl, propionyl, butyryl, isobutyryl, valeryl and isovaleryl.

The compounds of formula I form salts, for example acid addition salts with acids such as hydrochloric and hydrobromic acid, or alkali metal (e.g. sodium or potassium) or alkaline earth metal (e.g. calcium) salts. Such salts may be prepared in known manner.

Compounds of formula I were tested for anti-inflammatory activity by the following procedure based on Tonelli et al, *Endocrinology* 77, 625 (1965):

Sprague-Dawley female rats, weighing 60 to 70 grams, are used in groups of 10. Ear edema is induced by inuncting both sides of the ear with an irritant mixture. This mixture containing 1% croton oil, 20% pyridine, 5% water and 74% diethyl ether, with or without test compound, is applied only once and only to the right ear. Six hours later the animals are sacrificed; a 9 mm diameter portion of both ears is punched out with a cork borer and weighed. The anti-inflammatory activity of the test agent is assessed by expressing the percent of the difference in average weight increase between the ears of the control groups and of the treated group.

$$\% \text{ Inhibition} = 100 \times \frac{\left(\begin{array}{c}\text{Avg. inc. in wt. of}\\\text{test groups}\end{array}\right) - \left(\begin{array}{c}\text{avg. inc. in wt. of}\\\text{controls}\end{array}\right)}{\left(\begin{array}{c}\text{Avg. inc. in wt. of}\\\text{controls}\end{array}\right)}$$

Results found for representative compounds of formula I are tabulated below, together with results found in 3 tests for the preferred compound reported by Brown et al in J. Med. Chem.(loc-cit) namely 4-(p-chlorophenyl)-2-phenylthiazole-5-acetic acid (B):

| Compound of formula I | Dose | % Inhibition |
|---|---|---|
| R = COCH$_3$ | 50 μg | −14% |
| | 500 μg | 41% |
| | 2.5 mg | 85% |
| | 5 mg | 100% |
| R = COC$_4$H$_9$ | 50 μg | 41% |
| | 500 μg | 54% |
| | 2.5 mg | 71% |
| | 5 mg | 87% |
| (B) | 50 μg | −30, 15, −7% |
| | 500 μg | 10, 35, 52% |
| | 2.5 mg | 93, 79, 89% |
| | 5 mg | 92, 93, 93% |

The compounds all show marked anti-inflammatory activity of about the same order. Surprisingly 4-substitution by an acyloxy group did not reduce anti-inflammatory activity.

This invention also provides processes for preparing compounds of formula I. Such processes are outlined in U.K. Patent Specification Nos. 1,145,884 and U.K. Pat.

No. 1,262,292. Accordingly this invention provides a process for preparing a compound of formula I or an acid addition salt thereof which comprises (a) reacting an α-haloketone of general formula:

wherein hal is a halogen atom, with a thioamide of general formula:

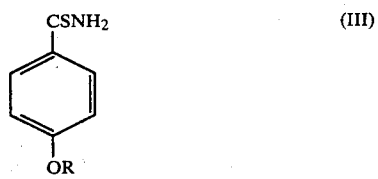

wherein R is as hereinbefore defined, or (b) dehydrating a compound of formula

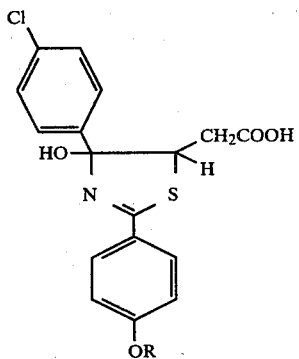

wherein R is as hereinbefore defined to give a corresponding compound of formula I, or (c) acylating a compound of formula I wherein R is hydrogen to give a compound of formula I wherein R is an acyl group, or Methods for carrying out processes (a) and (b) above are extensively described in our U.K. Patent Specification Nos. 1,145,882 and 1,262,292.

Acylation of a compound of formula I wherein R is hydrogen may be effected by standard methods using an acylating agent comprising an acyl R moiety, such as an anhydride or acyl halide, e.g. chloride.

The invention provides a pharmaceutical composition comprising a compound of general formula (I) or a pharmaceutically acceptable salt thereof in association with a pharmaceutically acceptable carrier. Any suitable carrier known in the art can be used to prepare the pharmaceutical composition. In such a composition, the carrier is generally a solid or liquid, or a mixture of a solid and a liquid. In some aerosol compositions the carrier may be a gas.

Solid form compositions include powders, granules, tablets, capsules (e.g. hard and soft gelatin capsules), suppositaries and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid from compositions include, for example, solutions, suspensions, emulsions, syrups, elixirs and pressurized compositions. The active ingredient, for example, can be dissolved or suspended in a pharmaceutically acceptable liquid carrier such as water, an organic solvent, a mixture of both or pharmaceutically acceptable oils and fats. The liquid carrier can contain other suitable pharmaceutical additives such as solubilizers, emulsifiers, buffers, preservatives, sweetners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glyceroland glycols) and their derivatives, and oils (e.g. fractionated coconut oil and arachis oil). For parental administration the carrier can also be an oily ester such as ethyl oleate and isopropyl myristate. Sterile liquid carriers are used in sterile liquid form compositions for parental administration. The liquid carrier for pressurized compositions can be a halogenated hydrocarbon or other pharmaceutically acceptable propellent.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg. or less to 750 mg. or more, according to the particular need and the activity of the active ingredient. The invention also includes the compounds in the absence of the carrier where the compounds are in unit dosage form.

The present invention also provides a semi-solid or aerosol pharmaceutical composition for topical administration comprising a compound of formula I or a pharmaceutically acceptable salt thereof in association with a pharmaceutically acceptable topical carrier.

By a 'semi-solid pharmaceutical composition' is meant an ointment, cream, salve, paste, jelly or other pharmaceutically or cosmetic composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Preferably, the topical compositions of the present invention contain from about 0.1% to about 20% by weight of the active ingredient. The compositions may, for example, contain from about 0.5% (preferably from about 1%) to about 10% by weight of the active ingredient.

The carrier used in the topical compositions of the present invention may be any carrier suitable for preparing topical semi-solid compositions or topical aerosol compositions. Examples of suitable carriers for semi-solid compositions are given in Lachman, Lieberman and Kanig (loc-cit) and in Chapter 67 of Remington's Pharmaceutical Sciences, (loc-cit). The carrier for the semi-solid composition may be, for example an emulsion base of the oil in water class (e.g. an emulsion of soft and liquid paraffins in water). Alternatively, the carrier may be an absorption base (e.g. a mixture of wool fat and soft paraffin). A third class of suitable carriers are water miscible bases (e.g. mixtures of high and low molecular weight polythene glycols).

When the composition is in aerosol form for topical administration, the composition may comprise the active ingredient and an easily liquifiable gas. Examples of such liquifiable gases are halogenated hydrocarbons and liquified lower hydrocarbons, both of which are well known as propellants in the aerosol art. (By "lower hydrocarbon" is meant a hydrocarbon containing up to six carbon atoms).

In addition to the active ingredient and the carrier base, the compositions of the invention may contain other ingredients such as antioxidants, buffers, emulsifying agents, perfumes, preservatives and solvents which confer on the product properties desirable in a topical formulation. In particular, buffers may be employed to adjust the pH of the composition to within the range of, for example 4 to 5.5 (e.g. 4.8) to maintain the active ingredient in its free acid form. The compositions can also contain other active ingredients.

In a further aspect, the invention provides a method of treating inflammation in warm blooded non-human animals which comprises topically administering to the animal an anti-inflammatory effective amount of a compound of formula I. By "topically administering" is meant administering to the exterior skin surface. The active ingredient may be administered in the form of a composition of the present invention.

EXAMPLE 1

2-(4-Acetoxyphenyl)-4-(4-chlorophenyl)thiazole-5-acetic acid (a) 3-Bromo-3-(4-chlorobenzoyl)propionic acid (27 g), and 4-hydroxy-thiobenzamide (14.6 g) were heated to 80° in dimethylformamide (50 ml). The reactants were kept at this temperature for 1 hour, cooled and poured on to ice. The resulting gum solidified, and was filtered, and washed with water, to give 31.6 g of powder, m.p. 184°–194° C. (decomp.) This was recrystallised from aqueous isopropanol affording 25.4 g of 4-(4-chlorophenyl)-2-(4-hydroxyphenyl) thiazole-5-acetic acid, hemihydrate, m.p. 192°–194° (d).

EXAMPLE 2

(b) 4-(4-Chlorophenyl)-2-(4-hydroxyphenyl)-thiazole-5-acetic acid (7.0 g, 0.016 moles) was dissolved in 0.1 N sodium hydroxide (493 ml, 0.372 moles) and cooled to 0° C. Acetic anhydride (1.5 ml, 0.016 moles) was added and the mixture left standing at room temperature for 3 hours. To the solution was added dilute hydrochloric acid and the resulting precipitate was filtered off, washed with a little water, dried and recrystallised from methylethylketone to give the title compound as a colourless solid (2.4 gm), m.p. 177°–180° C.

Analysis Found: C, 58.94; H, 3.87; N, 3.43%. $C_{19}H_{14}ClNO_4S$ requires: C, 58.84; H, 3.64; N, 3.61%.

EXAMPLE 3

4-(4-Chlorophenyl)-2-(4-Valeryloxyphenyl)thiazole-5-acetic acid

4-[4-Chlorophenyl]-2-[4-hydroxyphenyl]thiazole-5-acetic acid (3.81 g, 0.11 moles) was dissolved in 0.2 N sodium hydroxide (55 ml, 0.027 moles) and cooled to 0° C. Valeryl anhydride (2.0 g, 0.011 moles) was added and the reaction flask shaken vigorously for 4 minutes. Dilute hydrochloric acid was added, and the resulting gum extracted into chloroform. The chloroform layer was washed with water, separated, dried over magnesium sulphate to give a white solid. The solid was stirred with water at about 50° C. for ¼ hour, filtered and dried to give the title compound as a colourless solid (3.68 g), m.p. 197°–9° C.

EXAMPLE 4

4-(4-Chlorophenyl)-2-(4-acetoxyphenyl)thiazole-5-acetic acid

In a similar manner to Example 1(a), 3-Bromo-3-(4-chlorobenzyl)propionic acid and 4-acetoxy-thiobenzamide are reacted in dimethylformamide solvent to give the title compound.

EXAMPLE 5

4-(4-Chlorophenyl)-2-(4-valeryloxyphenyl)thiazole-5-acetic acid

3-Bromo-3-(4-chlorobenzyl)propionate acid and an equimolar amount of 4-valeryloxythio-benzamide are stirred in isopropyl alcohol solvent containing sodium carbonate to give 4-(4-chlorophenyl)-4-hydroxy-2-(4-valeryloxyphenyl)-2-thiazolin-5-acetic acid. This compound is dehydrated by heating to give the title compound.

I claim:

1. A compound of formula

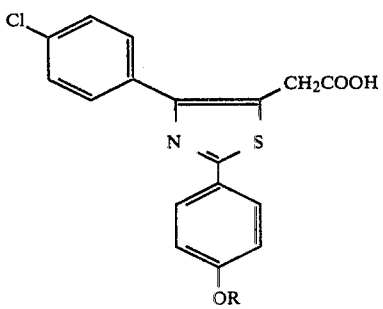

(I)

or a pharmaceutically acceptable salt thereof, wherein R is alkanoyl of 2 to 7 carbon atoms.

2. A compound as claimed in claim 1 which is 2-(4-acetoxyphenyl)-4-(4-chlorophenyl)thiazole-5-acetic acid or a pharmaceutically acceptable salt thereof.

3. A compound as claimed in claim 1 which is 4-(4-chlorophenyl)-2-(4-valeryloxyphenyl)thiazole-5-acetic acid or a pharmaceutically acceptable salt thereof.

4. A pharmaceutical composition comprising an anti-inflammatory effective amount of a compound of formula I as claimed in claim 1 or a pharmaceutically acceptable salt thereof and a pharmaceutically acceptable carrier.

5. A pharmaceutical composition as claimed in claim 4 which is in semi-solid or aerosol form for topical application.

* * * * *